(12) United States Patent
Bousquet

(10) Patent No.: US 7,935,091 B2
(45) Date of Patent: May 3, 2011

(54) CATHETER EXTENSION SET AND CLOSURE ASSEMBLY THEREFOR

(76) Inventor: Gerald G. Bousquet, Tyngsborough, MA (US)

( * ) Notice: Subject to any disclaimer, the term of this patent is extended or adjusted under 35 U.S.C. 154(b) by 1135 days.

(21) Appl. No.: 11/653,748

(22) Filed: Jan. 16, 2007

(65) Prior Publication Data

US 2008/0172007 A1 Jul. 17, 2008

(51) Int. Cl.
*A61M 5/14* (2006.01)
(52) U.S. Cl. ........................................ 604/256
(58) Field of Classification Search .............. 604/236, 604/256, 533–536, 538, 539, 905, 238; 138/89, 138/89.2; 222/525; 215/272, 273, 279, 292, 215/295, 296, 320, 358, 361, 362, 356
See application file for complete search history.

(56) References Cited

U.S. PATENT DOCUMENTS

| | | | |
|---|---|---|---|
| 2,670,869 A * | 3/1954 | Martin | ........................ 215/329 |
| 4,432,764 A | 2/1984 | Lopez | |
| 4,440,207 A | 4/1984 | Genatempo et al. | |
| 4,614,514 A | 9/1986 | Carr et al. | |
| 5,190,534 A | 3/1993 | Kendell | |
| 5,205,821 A | 4/1993 | Kruger et al. | |
| 5,694,978 A * | 12/1997 | Heilmann et al. | ............. 138/89 |
| 2005/0147525 A1 | 7/2005 | Bousquet | |

* cited by examiner

*Primary Examiner* — Kevin C Sirmons
*Assistant Examiner* — Catherine N Witczak

(57) ABSTRACT

A catheter end closure assembly includes a catheter adaptor with a head, a stem, a fastening segment between the head and stem and an axial passage extending the length of the adaptor. A plug with a head and a shank is shaped and dimensioned so that the shank may slidably engage in the stem and block a segment of the passage therein. The assembly also includes a cap dimensioned to be engaged around the stem and the fastening segment so as to define between the cap and adaptor a closed chamber that contains the stem and plug. Interfitting fastening surfaces on the cap and the fastening segment may releasably couple the cap to the adaptor, and cooperating surfaces on the plug and cap side wall may interfit when the cap is coupled to the adaptor so that when the cap is subsequently decoupled from the adaptor, the plug is automatically pulled from the passage. The assembly may be incorporated with a catheter extension set to facilitate dialysis or other therapy.

9 Claims, 2 Drawing Sheets

CATHETER EXTENSION SET AND CLOSURE ASSEMBLY THEREFOR

BACKGROUND OF THE INVENTION

1. Field of the Invention

This invention relates to medical catheters. It relates especially to a catheter extension set and an assembly for releasably terminating same in an aseptic manner.

2. Background Information

Patients who have kidney failure must be attached periodically to a dialysis machine through which the patient's blood is circulated and cleansed before being returned to the patient. This involves drawing blood from an artery of the patient through an arterial catheter connected to the dialysis machine and returning the cleansed blood to a vein of the patient via a venous catheter. In peritoneal dialysis, blood is drawn from and returned to the patient via the peritoneum. When a patient requires dialysis on a regular basis, the catheters are implanted in the patient with the proximal ends of those catheters being located outside the body and terminated by adapters or connectors, e.g. a Luer connector. Since those catheter connectors and the connectors on the dialysis machine are often made by different manufacturers, they may not be compatible. Therefore, a catheter extension set is often required to match the connector of each implanted catheter to the corresponding connector of the dialysis machine.

A typical extension set includes a length of flexible tubing having different connectors at its proximal and distal ends, the latter of which mates with the connector of the implanted catheter and the former of which is connectable to the dialysis machine. The set may also include a releasable clamp on the tubing for selectively stopping fluid flow therethrough. The catheter extension set usually remains connected to the catheter implanted in the patient.

Typically when a dialysis session is completed, the extension set is decoupled from the dialysis machine and the usual male connector at the proximal end of the set is closed by an end cap which is basically a blind or dead-end version of a female connector. Invariably prior to affixing the end cap, the male connector is sanitized or disinfected by wiping it down with a disinfectant such as alcohol, bleach or betadine. However, I have found through testing that even after such a wipedown, appreciable biological contamination still exists on the connector due to the fact that the connector has exterior threads and crannies which are difficult to reach with a disinfectant wipe. Resultantly, when the connector is again coupled to the mating connector of the dialysis machine, an administration set or other therapeutic apparatus, biological contaminants may be entrained in the fluid flow to the patient giving rise to infection and possible sepsis.

A variety of techniques have been used in an attempt to reduce the frequency of the infections described above. These have included impregnating the catheter connectors with antibiotic or photodynamic substances, incorporating silver or silver compounds in the connectors and irradiating the devices with infrared or ultraviolet light. Each of these prior techniques has, to some extent, reduced the frequency of infection. However, none of them is ideal. An ongoing concern is that microorganisms have the potential to develop resistance to antimicrobials incorporated into the catheter or device in an attempt to prevent infection. Thus, there is an on-going need for an improved mechanism for sanitizing the end fittings of medical catheters generally and catheter extension sets in particular.

SUMMARY OF THE INVENTION

Accordingly, it is an object of the present invention to provide an improved catheter extension set for use during dialysis.

A further object of the invention is to provide a closure assembly for terminating the proximal end of a catheter extension set in an efficient and aseptic manner.

Yet, another object is to provide a closure assembly for maintaining the sterility of a catheter connector.

Another object of the invention is to provide a closure assembly for a catheter connector or adaptor which is easy to connect to and disconnect from the associated connector or adaptor.

A further object of the invention is to provide a closure assembly of this type which is relatively easy and inexpensive to make in quantity.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, while my closure assembly may be used to terminate any medical catheter in an aseptic manner, it is especially adapted to terminate and close the proximal connector or adaptor of an otherwise conventional catheter extension set after the set has been disconnected from a dialysis machine, fluid administration set or other medical apparatus. The assembly, preferably presented in a sterile package, includes an adaptor plug which plugs into the end of, and closes, the passage in the adaptor stem. The cap has internal wall surfaces which interfit with the adaptor so that the cap and adaptor may be coupled together to form a fluid-tight enclosure or chamber containing the adaptor stem and plug. A sanitizing agent may be present in, or may be introduced into, the chamber so as to immerse the adaptor stem and plug therein in that agent for a long enough time to completely sanitize or disinfect them.

The end cap and its now sanitized contents may remain on the adaptor or connector until it is necessary to recouple the extension set to a dialysis machine, administration set or other therapeutic apparatus. When that time arrives, the closure assembly may be pointed downward and the cap decoupled from the adaptor such that the disinfecting agent remains in the cap.

In accordance with the invention, the cap and plug have interfitting surfaces so that the separation of the cap from the adaptor automatically removes the plug from the adaptor passage. The adaptor can then be reconnected to the dialysis machine or other apparatus in the usual way with assurance that there has no bacterial formation on the adaptor stem during its period of nonuse. The cap and now-attached plug are preferably disposable items and may be thrown away.

While my closure assembly is especially adapted to terminate an extension set, it should be understood that it can also be used to releasably close the connector at the end of any medical catheter in a fluid-tight aseptic manner.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
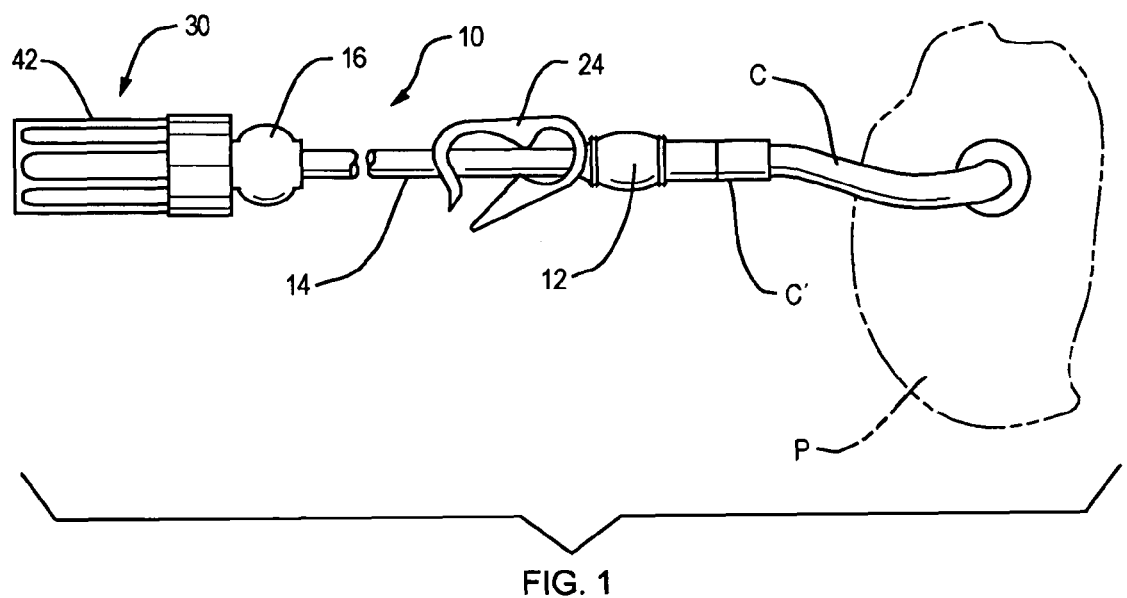
FIG. 1 is a diagrammatic view of an implanted catheter whose proximal end is connected to a catheter extension set incorporating a closure assembly according to the invention.

Referring to FIG. 1 of the drawings, a catheter C has its distal end implanted in a patient P. The proximal end of the catheter C has a connector or adaptor C' connected to one end of a catheter extension set shown generally at 10. The function of the extension set is to facilitate a connection between connector or adaptor C' and the connector of therapeutic apparatus such as a dialysis machine during a dialysis session, and to provide a sterile, leak-proof, releasable termination at the proximal end of catheter C between such sessions.

Figure 2:
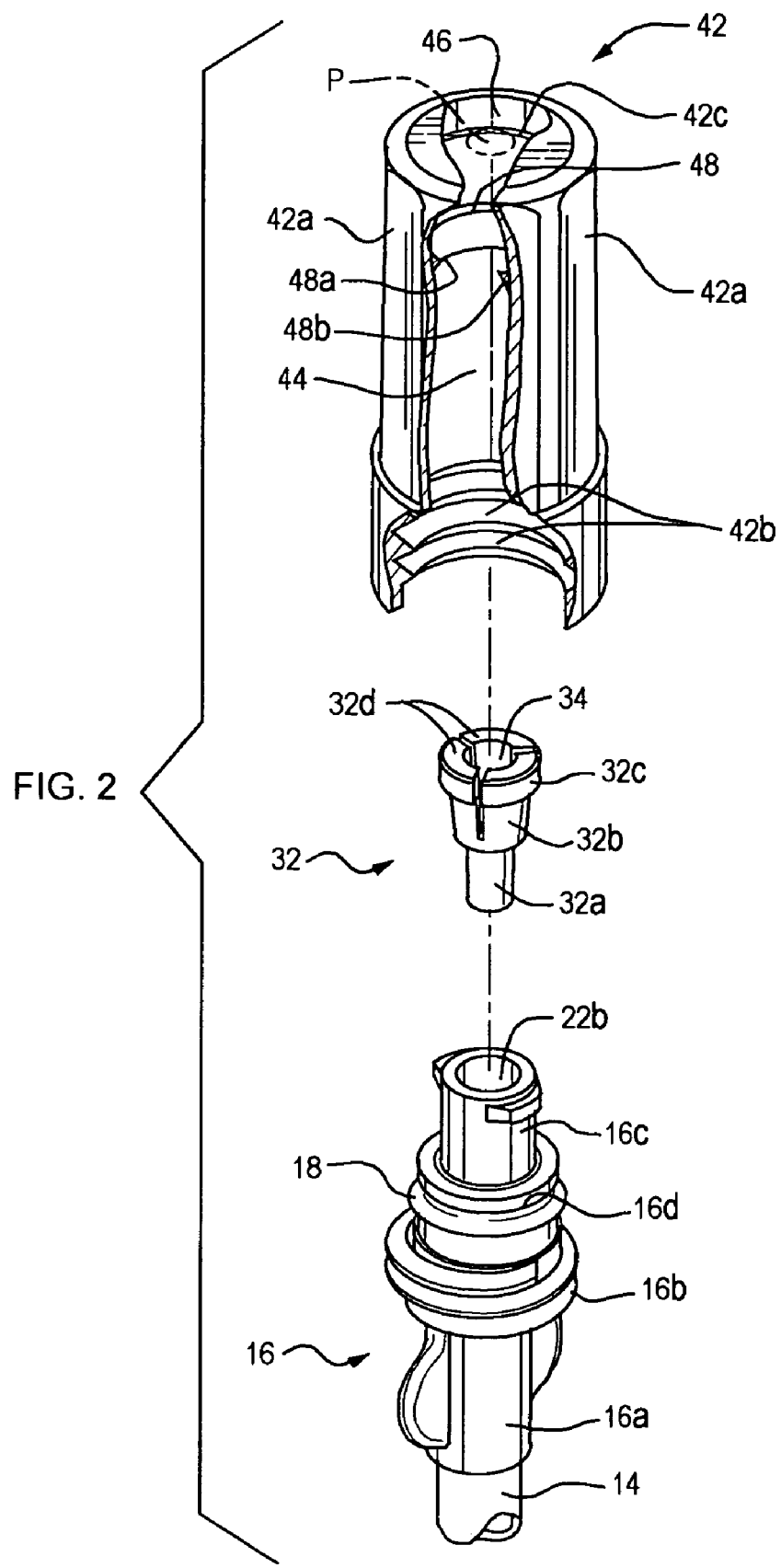
FIG. 2 is an exploded isometric view, on a larger scale, showing certain components of the FIG. 1 assembly in greater detail.

As shown in FIGS. 1 and 2, set 10 comprises a conventional connector or adaptor 12 which is secured to the distal end of a flexible tube 14. Adaptor 12 may be any one of a variety of known medical threaded or bayonet-type connectors; the illustrated one is a female Luer connector. The proximal end of tube 14 may be terminated by a standard adaptor 16, e.g. a male Luer connector. Adaptor 16 comprises a handle or head 16a, an exteriorly threaded segment 16b and a reduced diameter stem 16c. A circumferential sealing surface is present on adaptor 16 between its shank 16b and stem 16c. The illustrated sealing surface is an O-ring 18 seated in a groove 16d in the adapter. However, it could just as well be a raised bead on the adapter or some other conventional sealing structure.

Figure 3:
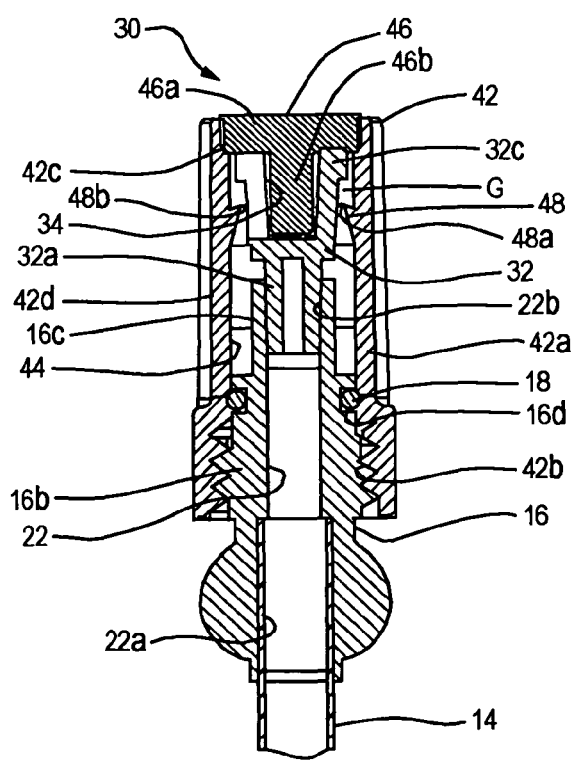
FIG. 3 is a longitudinal sectional view showing the FIG. 2 components as assembled.

As best seen in FIGS. 2 and 3, adaptor 16 is formed with an axial passage 22 which extends the entire length of the adaptor. A segment 22a of that passage that is located in head 16 is enlarged to accommodate a proximal end segment of catheter 14. That segment is bonded to the passage wall to create a fluid-tight connection therewith. Also, a segment 22b of passage 22 that extends within the adaptor stem 16c has the usual axial taper.

Preferably set 10 includes a releasable clamp 24 (FIG. 1) engaged on tube 14 to stop fluid flow through the tube selectively as will be described later.

Still referring to FIGS. 2 and 3, extension set 10 also includes a closure assembly shown generally at 30 for releasably capping adaptor or connector 16 in a fluid-tight aseptic manner. Assembly 30 comprises a plug 32 having a shank 32a which is sized and axially tapered to wedge into the tapered passage segment 22b in the adaptor stem 16c thereby blocking the passage 22. Shank 32a may be solid or partially hollowed out as shown to save material. Plug 32 also has a head 32b at the proximal end of shank 32a whose free end is formed with a circumferential flange 32c. As best seen in FIG. 2, the illustrated head 32b has an axial passage 34 and is slitted lengthwise to divide the head into a plurality, herein three, of slightly spaced-apart flexible, resilient tines 32d each of which includes a sector of flange 32c at its proximal end for reasons that will become apparent.

The remaining component of closure assembly 30 is a generally cylindrical cap indicated at 42. Cap 42 includes a tubular cylindrical side wall 42a having an axial passage 44. A distal end segment of wall 42a is internally threaded 426 to threadedly engage the threaded segment 16b of adaptor 16. The proximal end of passage 44 is permanently closed by a recessed cover 46 secured to the proximal end of the side wall 42a. More particularly, as best seen in FIGS. 2 and 3, the proximal end segment of cap passage 44 is counterbored to form a shoulder 42c, and the cover 46 has a discoid section 46a which is bonded to that shoulder.

Although not essential in all applications, cover 46 preferably also includes a post 46b which extends axially from section 46a into the interior of the cap wall 42a. Post 46b is shaped and arranged so that when it is inserted into and seated in the passage 34 in plug 32 as shown in FIG. 3, it prevents the plug tines 32d from flexing radially inward. In other words, it positively prevents any reduction in the diameter of the plug head 32b or its flange 32c.

Although the illustrated cap 42 is shown as having a separate end cover 46 which is bonded or welded to housing 42a, that cover could be formed integrally with housing 42a at the same time the housing is formed.

Still referring to FIGS. 2 and 3, the cap side wall 42a has an internal radial detent 48 spaced axially from shoulder 42b. The illustrated detent is a single circular shelf whose inside diameter at edge 48a is smaller than the outside diameter of the plug flange 32c. The circular detent could also be interrupted, i.e. three or more detents may be distributed about the cap axis and define a collective edge 48a. Preferably, detent(s) 48 has an underside 48b which inclines from wall 42a to edge 48a. The cap 42 is arranged so that when the plug 32 is inserted into the passage segment 22b of adaptor 16 as shown in FIG. 3 and cap 42 is engaged on the adaptor 16, the tapered underside 48b of detent 48 will be pressed against the top of the plug thereby squeezing the plug tines 32d radially inward so that the diameter of flange 32c becomes smaller than that of edge 48a enabling the flange to slide past the detent. When the flange clears the detent, the tines will resume their normal unstressed positions again making the flange diameter larger than that of edge 48a so that the plug and cap become interconnected. At this point, cap 42 may be turned down tightly onto the threaded segment 16b of adaptor 16. When the cap is tight, its cover section 46a engages the top of plug 32 thereby holding the plug tightly in passage 22 as shown in FIG. 3.

When cap 42 tightened onto adaptor 16, the sealing surface 18 makes a sliding seal with the cap wall 42a thereby forming a fluid-tight chamber between the adaptor 16 and cap 42 that contains the adaptor stem 16c and the plug 32 therein. Preferably, cap 42 has exterior knurls 42d to facilitate turning the cap. As will be described, that chamber may be filled with a sterilizing agent.

When it becomes time to reuse the extension set 10, cap 42 may be unscrewed from adaptor 16 to expose the stem. As the cap is being unscrewed, the internal detent 48 of cap 42 engages under the flange 32c of plug 32 and pulls the plug shank 32a from the passage segment 22b. Thus, as the cap 42 is being disengaged from adaptor 16, the plug 32 is automatically separated from the adaptor when the detent 48 engages the underside of the flange 32c. Preferably, the assembly 30 parts are dimensioned so that when the cap assembly 30 is assembled to the adaptor 16 as shown in FIG. 3, a small clearance or gap G is left between detent 48 and flange 32c to ensure that the plug shank 32a plugs tightly into the passage segment 22b in adaptor 16 before the cap cover 46 engages the top of plug 32. In other words, the gap G allows for tolerance variations in the assembly parts.

Preferably, adaptor 16, plug 32 and cap 42 are all made of a suitable medical grade sterilizable plastic material, one example being Basell Pro-fax PD626 polypropylene.

As noted above, the extension set 10 may be used when patient P is undergoing dialysis from a dialysis machine. After each dialysis session, each extension set 10 is disconnected from the dialysis machine and must be closed in an aseptic manner to stop any blood flow from the patient and to prevent sepsis. In accordance with my invention, this is accomplished by closing clamp 24 to prevent fluid flow to and from the patient and disconnecting adaptor 16. Then a nurse obtains a closure assembly 30 which may be stored in a sterile bag B. He/she opens the bag and, wearing sterile gloves, removes plug 32 and plugs its shank 32a into the open end of the passage segment 22b in adaptor 16 to block passage 22. Next, the cap 42 is removed from the bag, oriented so that its open end faces up and filled with an antiseptic agent such as betadine or alcohol. Then the adaptor 16 is screwed down into the cap so that the adaptor stem 16c and plug 32 are bathed in that solution. The antiseptic agent is free to flow into the set 10 down to clamp 24. As the cap 42 is being coupled to the adaptor, the segmented plug flange 34c snaps under the detent 48 as described above thereby locking the cap to the plug. Thus, when it again becomes time to expose the end of adaptor 16 in order to reengage the patient P to the dialysis machine for another dialysis session, the plug 32 will be disengaged automatically from the adaptor 16 as the cap 42 is unscrewed from the adaptor. In other words, as the cap 42 is pulled away from the adaptor, the internal detent 48 of the cap will engage the plug flange 32c and pull the plug out of the adaptor passage 22. After drawing away any residual sterilizing agent in tube 14, connector 16 may be reconnected to the dialysis machine and the clamp 24 released to enable fluid flow to or from the patient via the extension set.

Although the closure assembly 30 could be sterilized and reused, it is preferably discarded and replaced by a new bagged aseptic assembly which may be attached to the adaptor 16 after the next dialysis session.

The illustrated cap 42 is a non-vented cap. It is also possible to use a vented cap in assembly 30. Such a cap includes a port or septum in the closed end of the cap as shown in phantom at P in FIG. 2 through which an antiseptic solution may be injected after the cap is secured to the adaptor 16. A cap such as this disclosed in my patent publication No. US-2005-0147524-A1, the entire contents of which is hereby incorporated herein by reference.

It will thus be seen that the objects set forth above, among those made apparent from the preceding description, are efficiently attained. Also, certain changes may be made in the above constructions without departing from the scope of the invention. For example, the detent(s) 48 of the cap 42 may interfit with the plug head 32b in other ways to effect removal of the plug from passage 22 when the cap is decoupled from the adaptor 16. For example, detent(s) 48 may be formed as a resilient clip(s) which snaps under the plug head when the cap is coupled to the adaptor. Alternatively, the plug head may be of a resilient material that is compressed by a rigid detent(s) 48 when the cap is coupled to the adaptor. Therefore, it is intended that all matter contained in the above description or shown in the accompanying drawing shall be interpreted as illustrative and not in a limiting sense.

It is also to be understood that the following claims are intended to cover all of the generic and specific features of the invention described herein.

The invention claimed is:

1. A catheter end closure assembly comprising
   a catheter adaptor including a head, a stem, a fastening segment between the head and stem and an axial passage extending the length of the adaptor;
   a plug including a head and a shank extending from the head, said shank being shaped and dimensioned to slidably engage in said stem and block a segment of said passage therein;
   an elongated cap having an open end, a closed end and a side wall extending between said ends, said cap being dimensioned to be engaged around said stem and said fastening segment so as to define between the cap and connector a closed chamber that contains the stem and plug;
   interfitting fastening surfaces on said cap and on said fastening segment for releasably coupling the cap to the adaptor, said interfitting surfaces comprising a resilient segment of the plug head and an interior rigid detent extending from the side wall of the cap at a location spaced from the closed end thereof, and
   cooperating surfaces on said plug and on said side wall which engage and interfit when the cap is coupled to the adaptor so that when the cap is subsequently decoupled from the adaptor, the plug is automatically pulled from the passage;
   wherein the resilient segment of the plug head defines a radial flange and is slitted lengthwise to form a plurality of spaced-apart resilient tines which may be compressed toward one another by said detent when the cap is coupled to the adaptor.

2. The assembly defined in claim 1 wherein
   the cap has a longitudinal axis, and
   the detent comprises at least one shelf centered on said axis and having an edge defining an area that is smaller than the natural cross-section of the plug head segment.

3. The assembly defined in claim 2 wherein the detent comprises a plurality of shelves distributed around said axis and collectively forming said edge.

4. The assembly defined in claim 1 wherein the detent has a surface facing the open end of the cap that is inclined from said side wall to said edge.

5. The assembly defined in claim 1 and further including a port in the cap for introducing a sterilizing agent into said chamber when the cap is coupled to the adaptor.

6. The assembly defined in claim 1 and further including a sealing surface encircling said adaptor between said fastening segment and said stem.

7. The assembly defined in claim 1 wherein
   the plug head has an axially extending hole therein, and
   further including a post projecting axially into the cap from the closed end thereof, said post being shaped and dimensioned to slidably engage in said hole when said cooperating surfaces of the plug and cap interfit to prevent radial compression of said tines.

8. A catheter extension set comprising
   a tube;
   a proximal connector at a proximal end of the tube;
   a distal connector at a distal end of the tube, and
   the closure assembly defined in claim 1 coupled to the proximal connector.

9. The extension set defined in claim 8 and further including a clamp releasably connected to the tube.

* * * * *